United States Patent
Ashby et al.

(10) Patent No.: US 9,042,621 B2
(45) Date of Patent: May 26, 2015

(54) INTRA-OPERATIVE SURGICAL PLAN CHANGING

(75) Inventors: Alan Ashby, Leeds (GB); Harald Bornfleth, Fuerstenfeldbruck (DE); Thorsten Burger, Leeds (GB)

(73) Assignee: DEPUY INTERNATIONAL LIMITED (GB)

( * ) Notice: Subject to any disclaimer, the term of this patent is extended or adjusted under 35 U.S.C. 154(b) by 325 days.

(21) Appl. No.: 13/503,253

(22) PCT Filed: Oct. 20, 2010

(86) PCT No.: PCT/GB2010/001939
§ 371 (c)(1),
(2), (4) Date: Jun. 25, 2012

(87) PCT Pub. No.: WO2011/051649
PCT Pub. Date: May 5, 2011

(65) Prior Publication Data
US 2012/0271613 A1 Oct. 25, 2012

(30) Foreign Application Priority Data
Oct. 27, 2009 (GB) .................................. 0918826.9

(51) Int. Cl.
G06K 9/00 (2006.01)
G06F 19/00 (2011.01)

(52) U.S. Cl.
CPC ................................... G06F 19/321 (2013.01)

(58) Field of Classification Search
None
See application file for complete search history.

(56) References Cited

U.S. PATENT DOCUMENTS

| 3,298,410 | A | * | 1/1967 | Morifuji | 81/458 |
|---|---|---|---|---|---|
| 3,816,855 | A | * | 6/1974 | Saleh | 623/20.31 |
| 3,901,298 | A | * | 8/1975 | Eby | 81/455 |
| 4,719,907 | A | * | 1/1988 | Banko et al. | 606/96 |
| 4,721,104 | A | * | 1/1988 | Kaufman et al. | 606/88 |
| 6,200,255 | B1 | | 3/2001 | Yu | |
| 8,160,345 | B2 | * | 4/2012 | Pavlovskaia et al. | 382/131 |
| 8,425,523 | B2 | * | 4/2013 | Aram et al. | 606/88 |
| 8,516,907 | B2 | * | 8/2013 | Stein et al. | 73/862.636 |

(Continued)

FOREIGN PATENT DOCUMENTS

| WO | WO 2008117057 A1 | 10/2008 |
|---|---|---|
| WO | WO 2009087214 A1 | 7/2009 |
| WO | WO 2009106812 A1 | 9/2009 |

OTHER PUBLICATIONS

PCT International Search Report PCT/GB2010/001939 dated Sep. 3, 2011.

(Continued)

*Primary Examiner* — Nancy Bitar (57) ABSTRACT

A system and computer implemented method for use in determining the deviation of an intra-operative position of an orthopaedic implant from a planned position is described. The position of the orthopedic implant in the bone is defined by a plurality of implant position parameters. The distance of a plurality of anatomical features in a three dimensional model of the surface of the bone relative to a model of the implant at a first position is calculated. The first position corresponds to a first set of values for the implant position parameters. The distance of the plurality of anatomical features to a model of the implant at a second position in the bone is calculated. The second position corresponds to a second set of values for the implant position parameters, and the second position is different to the first position.

20 Claims, 6 Drawing Sheets

(56) References Cited

U.S. PATENT DOCUMENTS

| | | |
|---|---|---|
| 8,721,568 B2* | 5/2014 | Rock et al. .................... 600/595 |
| 2006/0161052 A1* | 7/2006 | Colombet et al. ............ 600/300 |
| 2007/0218561 A1* | 9/2007 | Goldman ........................ 436/89 |
| 2007/0219561 A1 | 9/2007 | Lavallee |
| 2008/0319448 A1 | 12/2008 | Lavallee |
| 2009/0209884 A1 | 8/2009 | Van Vorhis |
| 2011/0071537 A1* | 3/2011 | Koga et al. .................... 606/103 |

OTHER PUBLICATIONS

GB Search Report 0918826.9 dated Mar. 1, 2010.

* cited by examiner

INTRA-OPERATIVE SURGICAL PLAN CHANGING

CROSS REFERENCE TO RELATED APPLICATION

This application is a National Stage 35 U.S.C. 371 of International Patent Application PCT/GB2010/001939 filed Oct. 20, 2010.

BACKGROUND OF THE INVENTION

The present invention relates to methods and apparatus for use in surgical procedures, and in particular to methods and apparatus which can be used intra-operatively to correct or update a planned position for an orthopaedic implant.

Surgical planning software can be used prior to an orthopaedic surgical procedure in order to help plan the intended position and orientation of the orthopaedic implant or implants in the patient's bone or bones. The intention of the surgical procedure is then to actually place the implant at its planned position. However, in practice, the actual position of implantation may vary from the planned position for a number of reasons. For example, in a hip replacement operation, the surgeon may plan to place the stem implant at a certain depth, varus-valgus angle and anteversion angle relative to the femur. However, these planned positions may be compromised by the reaming process resulting in a different implant position intra-operatively.

However, the surgeon may not be aware that the implant has not been placed at the planned position.

Hence, it would be beneficial if the surgeon could determine any variation in the intra-operative position compared to the planned position and so decide whether any corrective action might help bring the implant position closer to the planned position.

BRIEF SUMMARY OF THE INVENTION

According to a first aspect of the present invention, there is provided a computer implemented method for use in determining the deviation of an intra-operative position of an orthopaedic implant in a bone of a patient from a planned position of the orthopaedic implant in the bone of the patient. The position of the orthopaedic implant in the bone can be defined by a plurality of implant position parameters. The method can include calculating or determining the distance of each of a plurality of anatomical features present in a three dimensional model of the bone of the patient relative to a model or representation of the implant at a first position in the three dimensional model of the bone. The first position corresponds to a first set of values for the implant position parameters. The method can further include calculating or determining the distance of the plurality of anatomical features present in the three dimensional model to a model or representation of the implant at a second position in the three dimensional model of the bone. The second position corresponds to a second set of values for the implant position parameters, and the second position is different to the first position.

By using distances, or lengths of lines, of a plurality of anatomical features relative to the implant, and with the implant at different positions in the bone, data can be obtained which can be output or used in a variety of ways to help determine any differences between a planned position of the implant and an actual intra-operatively determined position of the implant. Hence, it can be determined whether to take any corrective action to try and more closely replicate the planned implant position.

For example, the distance, or length information, for the implant model at different positions in the bone model can be provided in a tabular form so that a surgeon can compare intra-operatively measured values of length (which are easier to measure than angles relative to hard to define axes or directions) with data in the tables to determine the extent to which the intra-operative position may have varied from the planned position.

The part of the implant to which distances are determined can be a unique and predefined position on the implant.

The number of anatomical features can be at least the same as, or greater than, the number of implant position parameters. Preferably, the number of anatomical features is at least the same as the number of main degrees of freedom of positional adjustment of the implant. The number of anatomical features can be three, at least three, or more than three. Preferably the number of anatomical features is five, at least five or more than five.

The implant position parameters can include at least one distance and/or at least one angle. The implant position parameters can include more than one distance and/or more than one angle. Preferably the implant position parameters include at least one distance and at least two angles.

The method can further comprise repeating the method for a range of values of each of the implant position parameters. The range of values can be defined by a maximum value, a minimum value and a step.

The method can further comprise outputting the values of the implant position parameters for each different position of the implant relative to the three dimensional bone model together with the corresponding distances from the implant to the plurality of anatomical features.

The values of the implant position parameters and the corresponding distances can be arranged in, stored in or output in a look up table. The values of the implant position parameters can be indexed by the distances. Hence, a user can use intra-operatively measured values for the distances to look up the implant position parameters which correspond to the intra-operative position of the implant and the intra-operative position can be compared with the planned position of the implant to identify or determine any differences.

The method can further comprise determining an indication of any differences between the planned position of the implant and the actual intra-operative position of the implant using the determined distances and distances that have been intra-operatively measured from the implant to the anatomical features of the bone of the patient Determining an indication of any differences can include identifying the calculated distances for an implant position that most closely match the measured distances for the implant position.

The method can further comprise determining the values of the implant position parameters corresponding to the most closely matching calculated distances.

The method can further comprise determining the differences between the values of the implant position parameters for the planned position of the implant and the values of the implant position parameters for the intra-operative position of the implant.

The method can further comprise outputting the differences between the values of the implant position parameters for the planned position of the implant and the values of the implant position parameters for the intra-operative position of the implant.

The method can further comprise automatically determining an adjustment to be made to the implant in order to, bring the intra-operative position of the implant closer to the planned position of the implant using the outputted differences.

The bone of the patient can be a femur. The implant can be a stem implant component.

The implant position parameters can include depth and/or varus-valgus angle and/or retroversion-anteversion angle.

The plurality of anatomical features can include at least three anatomical features selected from: the anterior aspect of the greater trochanter; the posterior aspect of the greater trochanter; the anterior ridge (also referred to as the superior aspect of the intertrochanteric line); the posterior ridge (also referred to as the quadrate tubercle on the intertrochanteric crest and referred to herein as the tubercle of the femur); and the lesser trochanter.

A further aspect of the invention provides a method for determining the intra-operative deviation from a planned implant position, comprising: generating a three dimensional model of at least the surface of a bone of a patient into which an implant is to be implanted, the three dimensional model including a plurality of anatomical features of the bone; creating a planned position of the implant in the patient's bone from the three dimensional model; calculating the distances from a part of the implant to the plurality of anatomical features for the implant at a plurality of different positions relative to the three dimensional bone model; and using the calculated distances and distances that have been intra-operatively measured from the implant to the anatomical features on the patient's bone to determine any differences in the planned position of the implant and the intra-operative position of the implant in the bone.

The method can be carried out entirely by a data processing device, such as a computer aided or assisted surgery system.

The method can further comprise tracking the position of a trackable instrument and calculating the distances that have been intra-operatively measured from the tracked positions of the trackable instrument.

The method can further comprise using an instrument to directly or indirectly measure the distance between the part of the implant and each of the anatomical features. The distances can be measured directly, for example using a caliper or similar instrument. The distances can be measured indirectly, for example by converting readings taken from or using the instrument and then deriving or calculating the distances from those readings.

The method can further comprise attaching a measurement instrument to the implant; and adjusting the measurement instrument to directly or indirectly measure the distance between the part of the implant and each of the anatomical features.

The method can further comprise adjusting the angular position and/or the length of at least a part of the instrument.

The method can further comprise using an electronic device which can track its own movements to directly or indirectly measure the distance between a reference point associated with the implant and the anatomical features. The electronic device can include one or more accelerometers and/or gyroscopes. The reference point can be a pre-defined position on, or part of, the implant.

The method can further comprise configuring an adjustable implant so as to compensate for or reduce a difference in the planned position of the implant and the intra-operative position of the implant in the bone.

A further aspect of the invention provides a computer readable medium storing computer program code executable by a data processing device to carry out any of the features of the method aspects of the invention.

A further aspect of the invention provides a computer assisted surgery system including a computer readable medium according to the preceding aspect of the invention.

A further aspect of the invention provides a system for determining the intra-operative deviation from a planned implant position, comprising: an instrument for measuring a distance from a part of an implant to a plurality of anatomical features of a bone of a patient in which the implant is located; and a computer assisted surgery system according to the preceding aspect of the invention.

The instrument can be an electronic device. The electronic device can track its own movements to directly or indirectly measure the distance between a reference point associated with the implant and the anatomical features. The electronic device can include one or more accelerometers and/or gyroscopes. The electronic device can calculate the distance measured between the reference point and an anatomical feature. The device can include an output, such as a display, for outputting the distance. The output can output the distance, e.g. by showing the distance on a display, as a user moves the device to an anatomical feature. The reference point can be a pre-defined position on, or part of, the implant.

The system may also include an adjustable implant. The configuration of the implant can be adjustable to allow the implant to be re-configured intra-operatively to allow the actual implanted position of the implant to more closely match the planned position of the implant.

BRIEF DESCRIPTION OF THE DRAWINGS

An embodiment of the invention will now be described, by way of example only, and with reference to the accompanying drawings, in which:

FIG. 6 shows a table illustrating an output from the data processing method illustrated by FIG. 5 and which can be used in the method illustrated by FIG. 1.

Similar items in different Figures share common reference numerals unless indicated otherwise.

DETAILED DESCRIPTION OF THE INVENTION

The invention will be described with reference to a particular stem implant as used in a hip replacement orthopaedic procedure. However, the invention is not limited to that specific application and the general principles of the invention taught herein can be applied to various types of implants and various types of orthopaedic procedures as will be apparent to the person skilled in the art from the following description.

Figure 1:
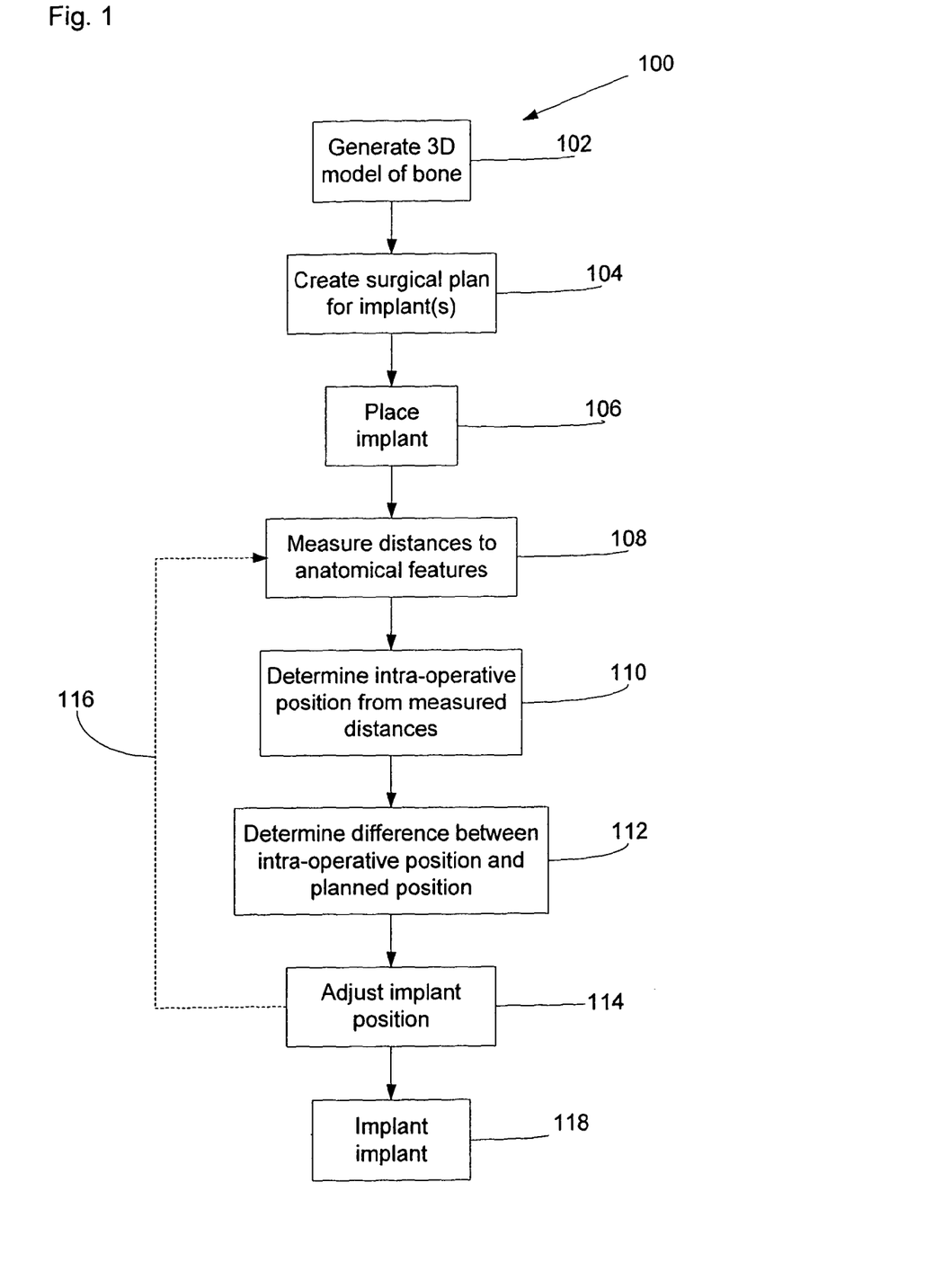
FIG. 1 shows a flowchart illustrating a method of intra-operatively checking and adjusting the position of an implant according to the invention.

FIG. 1 shows a flow chart illustrating a method 100 for intra-operatively changing or adjusting an implant to more closely match a pre-operative surgical plan.

The method begins with the generation 102 of a three dimensional model of the bone, or relevant portion of the bone, into which the implant is to be implanted. There are a number of ways in which the 3D model of the bone can be created and which are generally known in the art. For example, the 3D bone model can be generated from a three dimensional projection scan or imaging of the patient's bone (e.g. a CT scan) or from a statistical shape model instantiated using data collected by imaging the patient's bone, e.g. by X-ray projection images or ultrasound images. Additionally, or alternatively, the bone model can be generated intra-operatively by collecting anatomical data from the patient's actual bone, for example by tracking a pointer as the positions of anatomical features are collected and/or as the pointer is run over the surface of the bone to determine the local shape of the surface of the bone. Hence, the bone model can be generate pre-operatively or intra-operatively.

After the bone model has been created at step 102, a plan is created 104 for the surgical procedure. This generally includes determining the type, size and position of the orthopaedic implant or implants to be used to achieve the intended purpose of the surgery. As used herein, "position" includes the angular position or orientation of the implant. In the current example of hip replacement, planning can include determining the pre-operative centre of rotation of the patient's hip joint, generally corresponding to the centre of the femoral head when located in the acetabulum. The surgical plan may then include determining the type of implants to be used, e.g. the particular type of stem implant to be used in the femur and the type of cup implant, if any, to be used in the acetabulum. The plan may then include determining the size of implant components to be used in the patient, which may depend on a number of factors, such as the size of the patient's bones and the amount of available bone stock into which the implant can be placed. Once the type and size of implant have been determined, then the plan can include determining the position at which the components should be placed so as to satisfy the intended purpose of the surgery.

The "position" of the implant will generally be determined by a number of implant position parameters, including both the location in space relative to the patient's bone and also the angular orientation relative to the patient's bone. For example, for a femoral stem, the planned position of the implant may be determined by a combination of the depth of insertion of the stem along the local axis of the femur, the angular orientation in a varus-valgus direction and the angular orientation in retroversion-anteversion direction. Similarly the planned position of the acetabular cup may be defined by the depth of insertion of the cup into the acetabulum and the orientation of the cup as defined by the inclination and retroversion-anteversion. The planning software is therefore used to determine the positions that the implant components should ideally be placed in so as to create the intended-effect of the surgery. The plan is created 104 using the 3D bone model of the bones and may be created pre or intra-operatively, or partially pre and intra-operatively.

Once the surgical plan has been created at step 104, at some stage during the surgical procedure, e.g. after resecting the patient's bones and/or reaming cavities to receive the implants, trial versions of the implants, or the actual implants themselves (both generally referred to herein as "implants") can be placed in the bones in the positions resulting from the preparation of the bones. For example, for some femoral implant components, the femoral head is removed by resecting the proximal part of the femur and then a cavity is reamed in the remaining part of the femur to receive the femoral stem component. Then the stem implant component is placed in the reamed cavity at step 106. Owing to surgical skill or other factors, such as bone condition, the actual cavity reamed during the surgical procedure may mean that when the stem implant is placed in the cavity at step 106, the actual intra-operative position of the implant may differ from the planned position. For example, the depth of the stem may be too great or too small and/or the angular orientation of the implant may not be as planned in either or both of the varus-valgus or retroversion-anteversion directions. The present invention allows any variations from the planned position to be determined so that action can be taken intra-operatively to try and bring the actual implant position closer to the planned position.

Figure 2:
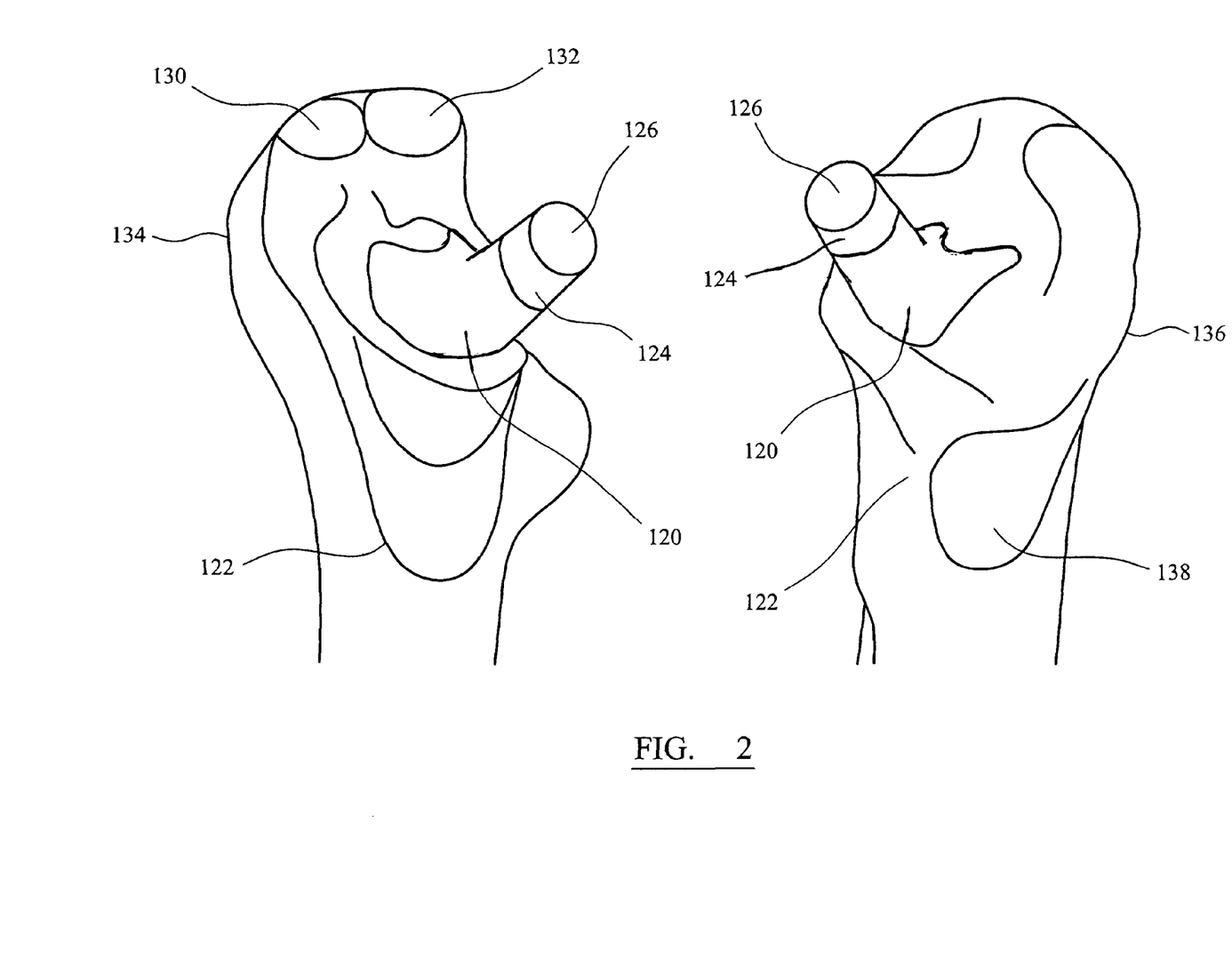
FIG. 2 shows perspective views of a proximal end of a femur with a stem component.

At step 108 the distances from a plurality of anatomical features of the bone in which the implant has been placed are determined. FIG. 2 shows a first view of a stem implant component 120 placed in a reamed cavity in the proximal part of a femur 122 from two different directions. The stem component includes an implant taper or neck part 124 to which a spherical head part of the femoral implant will later be attached. The distance between the same part of the implant, such as the centre of the top surface of the implant taper 126, is determined with respect to five anatomical features of the proximal part of the femur and which are therefore local to the implant. As illustrated in FIG. 2, the five anatomical features of the femur are the anterior aspect of the greater trochanter 130, the posterior aspect of the greater trochanter 132, the anterior ridge 134 (superior aspect of the intertrochanteric line), the tubercle of the femur 136 and the lesser trochanter 138.

These five distances can be measured in a number of ways. If a CAS system is being used which includes a tracking system for navigating instruments and implants, then the tracking system can be used to track and determine the position of a trackable pointer as its point is placed on the centre of the top surface of the implant taper 126 and each of the five anatomical points. Hence, the tracking system can then determine the five distances from the common point to each of the anatomical features of the femur.

Although it is preferred to measure five distances, in some embodiments fewer or more distances can be measured. Preferably at least three distances are measured so as to allow the three main degrees of freedom of the implant to be assessed (depth, varus-valgus angle and retroversion-anteversion angle). For example, the distances to each of the posterior aspect of the greater trochanter, the proximal aspect of the lesser trochanter and the anterior ridge can be used. Other anatomical features of the femur can also be used including the piriformis fossa and the gluteal tuberosity.

Figure 3A:
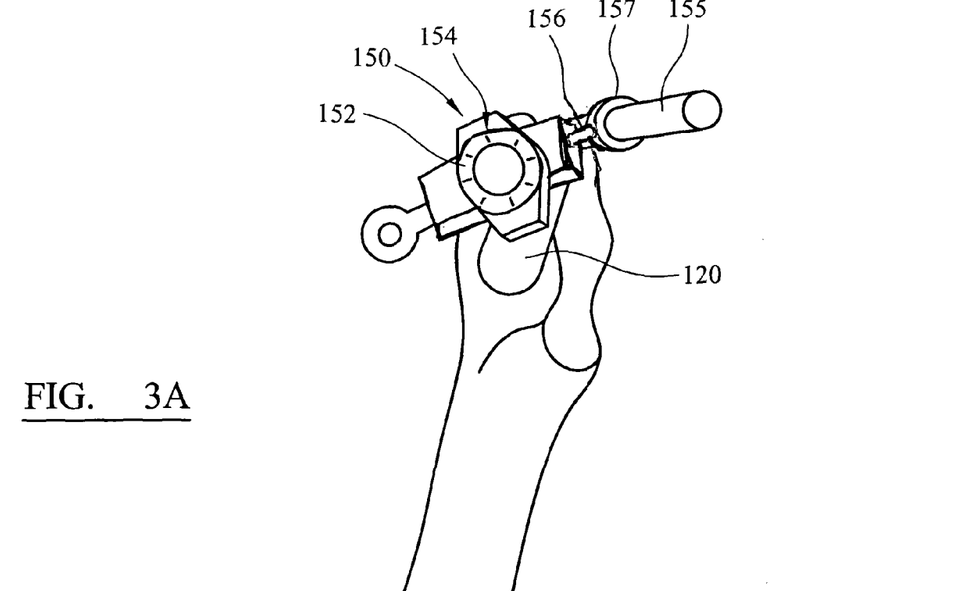
FIGS. 3A and 3B respectively show perspective views of an instrument which can be used in the method illustrated by FIG. 1.
Figure 3B:
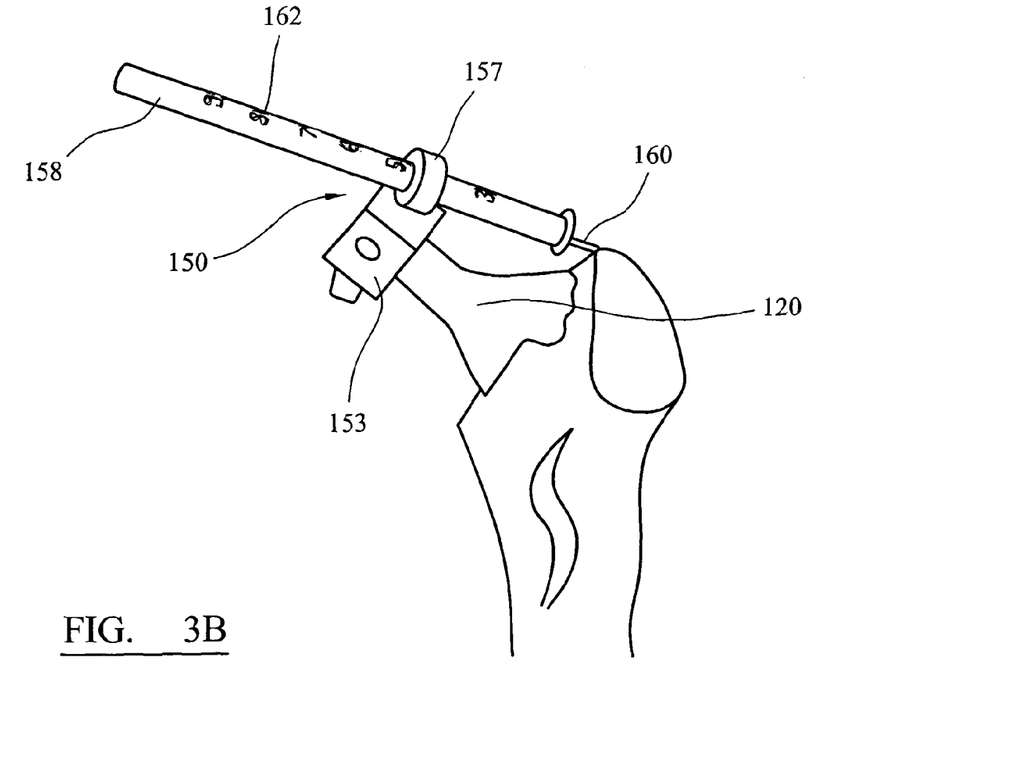

If no automatic mechanism to determine the plurality of distances is available, then a tool or instrument can be used to manually measure the plurality of distances from the implant to the anatomical features. For example FIGS. 3A and 3B show two different perspective views of a distance measurement instrument 150 placed on the implant taper of the stem implant 120. The body 152 of the instrument includes a circular aperture into which the implant taper of the stem has been inserted. Around the circular aperture are a plurality of markings which can be read to show the degree of rotation of the body of the instrument about the implant taper. A marking is provided on the upper surface of the implant taper to provide an origin or 'zero' marking which acts as a reference from which relative angles can be measured. A pivotable arm 156 extends from the body 152 bearing a loop 157 having a central aperture in which an elongate rod 158 is slidably mounted. A distal end of the rod bears a pointer 160 with a tip. A plurality of markings 162 extend along the longitudinal axis of the rod and which can be read to determine the length of the rod between the tip of the pointer and the loop by which the rod is attached to the body.

The instrument can be used to provide measurements by which the distance from the implant to the anatomical marks can be determined. The body of the instrument is rotated about the implant taper of the stem to bring the distal pointer bearing end of the rod close to the anatomical feature. The rod can be pivoted relative to the body about the arm 156 and the length of the rod can be adjusted by sliding the rod in the loop 157. The rod's length can be adjusted, the rod's angle relative to the body adjusted and the body of the instrument rotated about the implant taper until the tip of the pointer just touches the anatomical feature of interest. The user then reads off the length of the rod from the scale markings 162 along its length and also reads off the angle of rotation of the instrument body relative to the implant taper from the angular scale markings 154. Using simple geometry, the position from the point where the distance was measured can be calculated from the length of the pivotable arm 156 and the angle of rotation about the implant taper.

In another embodiment, angular information is not used and only the length of the rod 158 is measured from the instrument 150. Rod 158 is constrained to rotate such that there is always a right angle between rod 158 and pivot arm 156. This means that the distance from the centre of the taper head to the rod end can be determined using pythagoras' theorem and the known length of the pivot arm and the length of the rod as measured from loop 157 to its tip, for each anatomical feature.

Hence, in some embodiments of the invention just length or both angular and length information from an instrument can be used to determine the distance from a fixed point to each of the anatomical features and in other embodiments, the distances are determined directly by measuring the respective distances between the fixed point and the anatomical features (e.g. using a trackable pointer).

In another embodiment, an electronic device can be used as the instrument and which can itself track and determine the distances from a point relative to the implant (or on the implant) and the anatomical features. The device can included accelerometers, a microprocessor and a display. Input buttons or other control devices can also be included to allow the device to be instructed to start measuring a distance when it is placed at a pre-defined position (e.g. the centre of the top of the implant stem) and to determine the straight line distance when placed at an anatomical feature. The device can continuously output the distance by showing it on its display device, or can store a plurality of distance measurements in memory and then output them together as a data signal and/or via the display. The pre-defined position, can be a position relative to the implant rather than being a part or point of the implant itself. All that this does is introduce a constant off set distance from the pre-defined position to the centre of the stem from which each distance from the centre of the stem to the anatomical features can be calculated using simple geometry.

However, the distances are measured and determined at step 108, the plurality of distances are used at step 110 to determine the actual intra-operative position of the implant at step 110. Then the difference between the planned position and the actual intra-operative position is determined at step 112. The data processing method by which these steps are carried out will now be described in greater detail with reference to FIGS. 4 and 5.

Figure 4:
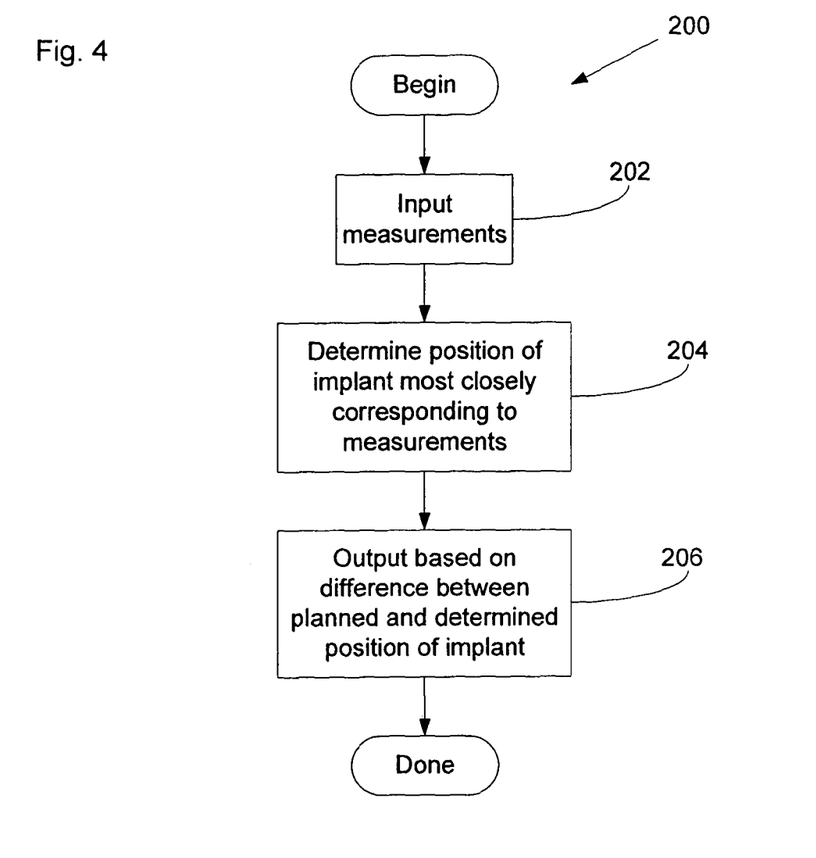
FIG. 4 shows a flow chart illustrating a method aspect of the invention at a high level.

FIG. 4 gives a high level overview of how the measured distance information can be used in a method 200 to determine intra-operatively how the actual implant position compares to the planned position. Depending on the specific embodiment, some steps of the method correspond to data processing steps, while in other embodiments can be manual tasks carried out by a person. The method uses intra-operative measurements of the position of a plurality of anatomical features relative to an intra-operatively positioned implant as "input" 202. As discussed above, the measurements can be taken using a variety of instruments and can be direct measurements of distance or measurements from which distance values can be calculated or otherwise derived. In some embodiments the measured values may be input to a data processing routine, or may simply be used as input to a manual or semi-manual method. Hence, the input measurements establish the intra-operatively determined position of the implant relative to a plurality of anatomical features of the patient's bone.

At 204 the method generally involved determining which of a plurality of possible positions of the implant in the patient's bone is closest to the actual position of the implant. This generally involves considering a model of the implant placed at a plurality of different known positions relative to the patient's bone, and then calculating distances, or some other positional metric, relative to the same anatomical features used to determine the intra-operative position of the implant. Then based on a comparison (direct or indirect) of the calculated distances and the measured distances, the one of the plurality of positions most closely matching the intra-operative position can be determined at step 204.

As the parameters defining the closest matching position are known, they can be approximated to the intra-operative position and hence the intra-operative position of the implant has been determined. Any difference between the intra-operative position parameters and the position parameters corresponding to the planned position of the implant can then be used to generate an output at step 206. The output may simply be the differences between the planned position and intra-operative position. Alternatively, or additionally, the output may be used for some secondary purpose, e.g. to adjust the implant or automatically determine a different implant to use as discussed in greater detail below. The output may be output to another computer program or software module or may be output used directly by a person, e.g. by being output in a visual or graphical form.

Figure 5:
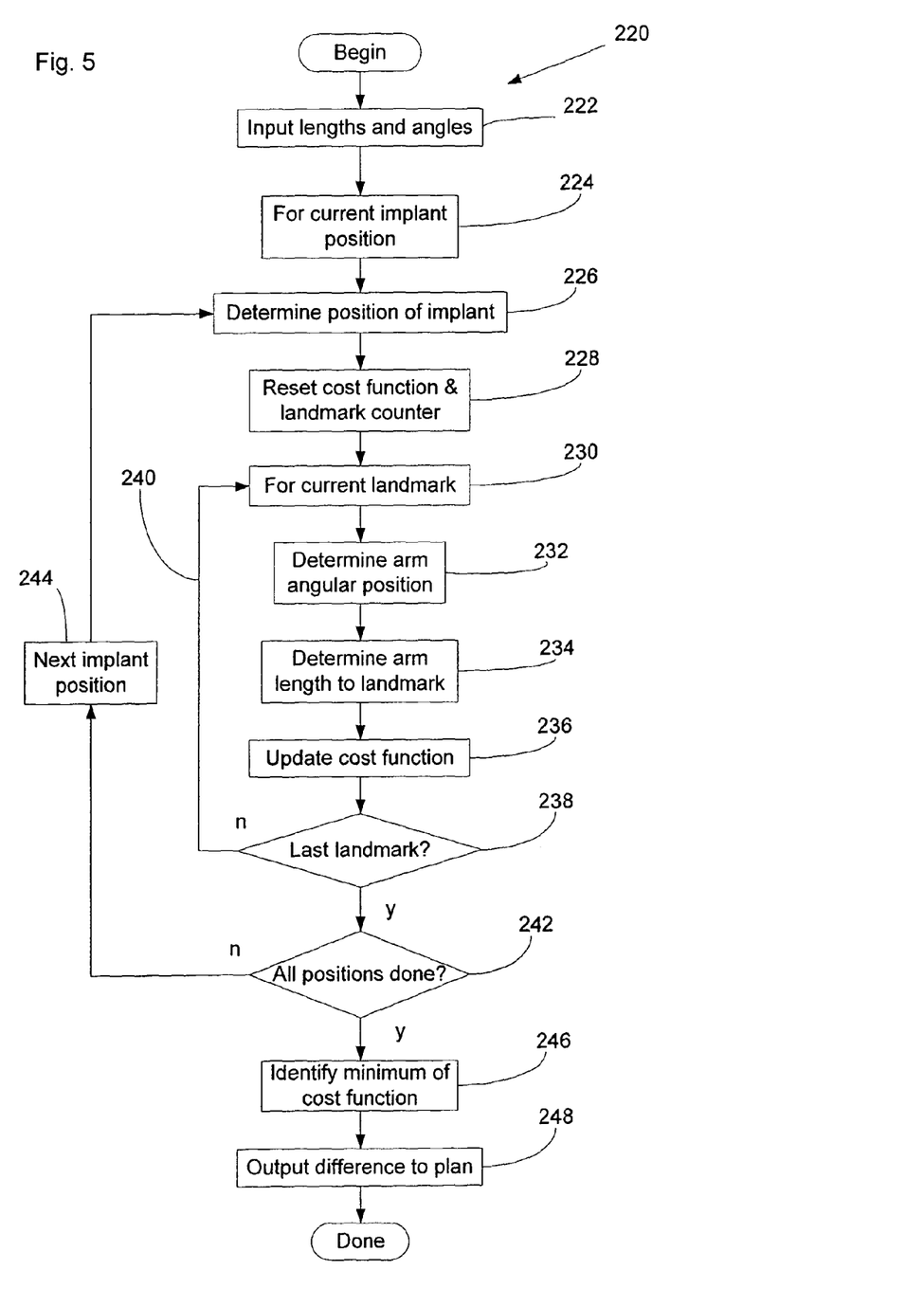
FIG. 5 shows a data processing flowchart illustrating a data processing method according to the invention.

FIG. 5 shows a flow chart illustrating an embodiment of a data processing method 220 by which distance or length information is used to determine any difference between the planned position of the implant and the actual intra-operative position of the implant. The position of the implant is determined by a number of implant position parameters. In the example case of a stem implant, those implant position parameters include its depth, varus-valgus angle and retroversion-anteversion angle. However, those positional parameters cannot easily or accurately be determined intra-operatively by direct measurement of their values.

Process 220 begins by taking as input at step 222 the five rod lengths and the five angles read from the instrument 150 as described above for the five anatomical features.

Then at step 224 a current set of implant position parameters is determined. The position of a model of the implant can be determined by a set of implant position parameters comprising its depth, varus-valgus angle and retroversion-anteversion angle.

In more detail, a maximum value, a minimum value and an increment value are specified for each of the implant position parameters. For example, for the stem depth a minimum value of −10 mm, maximum value of +10 mm (relative to some arbitrary origin) and a step value of +1 mm may be specified.

For each of varus-valgus and retroversion-anteversion a minimum angle, maximum angle and +1° increment may be specified. Then an initial value of each of these implant position parameters is set at step 224 and used in a first loop.

Then at step 226, using a model of the implant and its taper, the software determines the position of the centre of the taper for the 3D model of the implant at the current implant position (where position includes the angular position). At step 228, a cost function for the current implant position is set or reset to zero and an anatomical landmark counter is set or reset to zero. Then at step 230 a first of the five anatomical landmarks is selected for evaluation. At step 232, using a model of the instrument (which essentially defines the relationship between the centre of the stem and the centre of the loop through which the arm passes) the position of the arm of the instrument is calculated by virtual rotating the arm about the centre of the stem taper using the input angular value for the first anatomical feature. Then at step 234, the length that the rod of the instrument would have to have in order to touch the anatomical feature is calculated.

Hence, steps 232 and 234 calculate, for the current combination of implant position parameters, the length the rod should have, using a 3D bone model of the patient which includes the anatomical features, the model of the implant in the 3D bone model at the current combination of implant position parameters. For example, with the implant stem model at the initial position of −10 mm, varus-valgus minimum angle and retroversion-anteversion minimum angle in the 3D bone model, the length of the rod to the current anatomical feature is calculated, using also the model of the instrument. Information is stored and accessible by the software which specifies the properties of the instrument, such as the length of the arm and other size and geometric information about the instrument.

At step 236, the cost function for the current implant position is incremented by the square of the difference between the calculated length of the rod and the actual measured length of the rod.

At step 238 it is determined whether the currently evaluated landmark is the last landmark or not. If not, then process flow returns 240 and the process repeats for a next one of the anatomical landmarks. Hence, steps 232, 234 and 236 are carried out for all five anatomical landmarks resulting in a cost function for the current implant position which indicates how close the current model implant position is to the actual intra-operatively measured implant position. The value of the cost function is stored associated with its corresponding set of implant position parameters (not shown in FIG. 5) and then at step 242 it is determined whether all different combinations of implant positions have been evaluated. If not, then process flow proceeds to step 244 and a next set of implant position parameters is selected for evaluation. For example, the stem depth may be incremented by +1 mm and then the cost function calculated again with the same values for the varus-valgus angle and the retroversion-anteversion angle. Processing keeps looping until all combinations of implant position parameters have been considered and a corresponding cost function calculated for each combination.

Once all implant positions have been evaluated, then processing proceeds to step 246 at which the minimum cost function is identified and also the set of implant position parameters for that minimum value of the cost function. For example, a depth of +2 mm, varus-valgus angle of 35° and retroversion-anteversion angle of 42° might have produced the lowest cost function value and so are determined at step 246 as being the actual intra-operative value of the implant position parameters.

At step 248, the difference between the planned implant position parameters and the intra-operative implant position parameters can be determined and output simply by calculating the difference between the planned values and the intra-operative values.

Continuing with the present example, if the planned values were a depth of +5 mm, varus-valgus angle of 38° and retroversion-anteversion angle of 36°, then the differences would be +3 mm, +3° and −4°. This data can simply be output by display to the surgeon at step 248 or can be output and used in other ways as will be described in greater detail below.

Process 220 is specific to the instrument shown in FIGS. 3A and 3B. In an embodiment in which the distances from the implant to the anatomical features are measured directly, process 220 is adapted by removing steps 232 and 234 and modifying the cost function to include the directly measured distance from the taper centre to the anatomical feature and the corresponding calculated distance as will be apparent to a person of ordinary skill in the art from the description above.

Process 220 uses an exhaustive search approach to identifying the minimum value of the cost function. In other embodiments, the process can be varied to use other optimization approaches, such as, e.g., the Simplex method.

Returning to FIG. 1, if the difference data is simply displayed to the surgeon at step 220, then the surgeon can determine whether to adjust the implant in some way at step. 114. The surgeon may determine that the differences between the intra-operative position and planned position are sufficiently small so that no adjustment is required and so the implant can simply be implanted at step 118, either by replacing the trial with the actual implant or by permanently fixing the implant.

On the other hand, the surgeon may determine that the actual intra-operative position is too far from the planned position and so may decide to adjust the implant position. This can be achieved in a number of ways. For example, the stem cavity can be re-reamed to allow the depth of the stem to be adjusted, i.e. made deeper, or bone material can be added to the cavity to adjust the stem depth, i.e. made shallower. Alternatively, or additionally, the stem cavity can be re-reamed to change the angle of the stem in either or both directions.

Alternatively, or additionally, the implant itself can be adjusted in order to bring the actual intra-operative position closer to the planned position. For example, a different sized or shaped implant could be selected, e.g. having a longer implant taper or an implant taper at a different angle to the main body of the stem.

Additionally, or alternatively, an adjustable implant system can be used in which the implant geometry can be adjusted. For example, an anatomic hip system can be used including a stem with an implant taper, a variety of collars and a head in which the length of the implant taper and the off set of the head relative to the stem can be adjusted by using different collars. Such an adjustable implant is described in greater detail in International Patent Application No. PCT/GB2008/001057 (Publication No. WO 2008/117057) the disclosure of which is incorporated herein by reference for all purposes. Hence, using the difference data output by process 220, the surgeon can adjust the implant, for example by extending the length of the implant taper with the appropriate collar and/or by changing, the angular orientation by rotating the head relative to the implant taper about an eccentric axis using the appropriate collar. Hence, the adjustable implant allows the offset of the head from the implant taper axis to be changed as well as the implant offset along the implant taper axis so as to bring the actual head position closer to that planned.

Additionally, or alternatively, the output 248 from process 220 can be passed to another software module which automatically determines what adjustments to the implant should be made in order to reduce or minimise the differences between the intra-operative position and planned position. The software module may comprise an expert system or similar which includes data specifying how all the different combinations of stem, collar size, and head angle relate to the change of depth, varus-valgus and retroversion-anteversion of the implant. Then a simple search or lookup of this data using the differences output at step 248 can be carried out by the software module which can then output the stem, collar and angle of head rotation which will bring the implant position closer to the planned position. The surgeon can then adjust the implant accordingly at step 114.

For example, the software module can change the plan by exhaustively considering all combinations of available components that can be mounted on the implant stem, until the resulting centre of rotation of the femoral head component in the reference frame of the femur substantially matches, or most closely matches, the centre of rotation that was originally planned. The software can also indicate whether the change required is beyond that available in the range of components and can make suggestions as to the minimum changes in bone removal that are required to allow matching, or closest matching, components to be used.

As illustrated schematically in FIG. 1 by process return line 116, the surgeon can decide, after adjusting the implant, to measure the distances again with the adjusted implant to see the effect of the adjustments to the implant on correcting the surgical plan. Hence, method 100 can have an iterative element to help focus in on an optimised adjustment of the implant.

Alternatively or additionally, the invention can be implemented using a look up table to determine what changes to the implant can be used to bring the implant closer to the planned position. In this embodiment, the planning software used at step 104 is adapted to generate a table relating the lengths to be measured intra-operatively using the tool to settings for the adjustable implant.

So at step 104 of the method, after the planning software has generated the surgical plan, in a manner similar to that illustrated in FIG. 5, the planning software generates a table 250 similar to that illustrated in FIG. 6. The planning software has access to data specifying the 3D bone model, a model of the implant and also to the planned implant position. The planning software then calculates what the distances to the plurality of anatomical landmarks (which are present in the 3D bone model) would be, for the implant at a variety of positions defined by various combinations of depth, varus-valgus angle and retroversion-anteversion angle. In particular, the software determines the lengths for sets of variations of the depth, varus-valgus angle and retroversion-anteversion angle relative to the planned implant position. The results of these calculations are then output as a table as illustrated in FIG. 6.

Look up table 250 includes seven rows 252, each corresponding to a different measured distance (50 mm to 62 mm) from the implant to the lesser trochanter and seven columns 254, each corresponding to a different measured distance (38 mm to 50 mm) from the implant to the greater trochanter post. Each cell 256 of the table includes a set of three implant position correction values for each of four different measured distances (46 mm to 52 mm) from the implant to the anterior ridge. Each set of three implant position correction values tells the surgeon what changes to the depth, varus-valgus angle and retroversion-anteversion angle would be required in order to return the implant to the planned position, for the corresponding three distances measured intra-operatively using the measurement instrument.

Returning to FIG. 1, after the planning software has been used to plan the implant position and generate a version of table 250 specific to the patient's anatomy and the planned implant position, the method continues generally as described above.

Then at step 108, the surgeon measures the distances from the implant to the three anatomical features, the greater trochanter post, the lesser trochanter and the anterior ridge. If the instrument 150 shown in FIGS. 3A and 3B is used, then the distances from the centre of the implant taper to the anatomical features can be calculated using the Pythagorean formula for right angle triangles, namely that the distance is equal to the square root of the sum of the squares of the known pivot arm length and the measured length of the rod. Hence, the measured lengths from the rod are equivalent to the input data in step 202. These calculated distances can be used in creating the deviation values for the look up table 250. The look up table can itself refer to the measured rod length values for the surgeon's convenience. Then, the surgeon can determine the difference between the intra-operative position and planned position by a simple look up of table 250 (corresponding generally to method step 112). For example, if the distance to the lesser trochanter is 56 mm, and the distance to the greater trochanter is 44 mm (corresponding to table cell 258) and the distance to the anterior ridge is 52 mm, then the deviation from the planned position is zero for the depth, varus-valgus and retroversion-anteversion and hence the implant has been placed at the planned position.

However, if the distance to the lesser trochanter is 60 mm, and the distance to the greater trochanter is 40 mm (corresponding to table cell 260) and the distance to the anterior ridge is 50 mm, then the deviation from the planned position is +4 mm for the depth, +2° for varus-valgus and +1° for retroversion-anteversion and hence the implant position would need correcting to remove these deviations in order to be placed at the planned position. This could be achieved in part, or wholly, by any one or combination of, re-reaming the cavity in the femur, to reduce the depth error and embed the implant more deeply in the bone, changing the offset of the head component along the axis of the implant taper of the stem and/or adding an offset to the head component in a direction perpendicular to the axis of the implant taper of the stem. Hence, at step 114 any adjustments to the implant itself or the position of the implant can be made by the surgeon, before actually implanting the implant at step 118. The information derived by the surgeon from the table can be considered equivalent to the output step 206 of method 200.

If all distances are measured from the tip of the implant taper (e.g. by using a trackable pointer and a tracking system), then the look up table can be prepared prior to surgery. Alternatively, if the instrument 150 shown in FIGS. 3A and 3B is used, then the angles of rotation of the instrument may be defined prior to surgery, based on prior knowledge about the patient's anatomy. The angles are then defined prior to surgery in order to make it possible to reach each landmark with the measurement rod. This should be possible even if the implant is in slightly the wrong position. The look up table can then be calculated pre-operatively for this set of angles. The surgeon then dials in the angles to the instrument 150 during surgery, performs the distance measurements, and finds the corresponding distance values using the lookup table. In both scenarios, the surgeon can determine the difference.

Although the above generally describes the invention being applied to a hip joint component, it will be appreciated that it can also be applied to other orthopaedic implant components, such as knee and shoulder components.

Also although the above generally describes the invention using a pre-defined point as being the centre of the stem of the implant, it will be appreciated that other points or parts of the implant can be used. Also, the pre-defined point does not have to be a part of the implant itself. Rather, it can be a point simply having a known positional relationship to the implant. This simply introduces an off set. All that is required is that the positions of the anatomical features can be determined relative to the actual intra operative implanted implant and also that the positions of the anatomical features in the 3D bone model relative to the model implant at different positions in the 3D bone model of the patient can be determined (either directly or indirectly).

Hence, the present invention provides various mechanisms by which the surgeon can take intra-operative measurements of the position of an implant or trial, relative to a plurality of anatomical features and then use information derived from those measurements to determine how close the intra-operative position is to a planned position. Hence, the surgeon can determine what action to take, if any, in order to bring the actual implant position closer to the planned position. This can improve the outcome of surgical procedures by intra-operatively checking how closely the result of the procedure will meet the planned result.

The invention claimed is:

1. A computer implemented method for use in determining the deviation of an intra-operative position of an orthopedic implant in a bone of a patient from a planned position of the orthopedic implant in the bone of the patient, wherein the position of the orthopedic implant in the bone is defined by a plurality of implant position parameters, comprising the steps of: calculating a first set of distances, the first set of distances being measured from a plurality of anatomical features present in a three dimensional model of at least a surface of the bone of the patient relative to a model of the implant at a first position in the three dimensional model of the bone, the first position corresponding to a first set of values for the implant position parameters; calculating a second set of distances, the second set of distances being measured from the plurality of anatomical features present in the three dimensional model to a model of the same implant at a second position in the three dimensional model of the bone, the second position corresponding to a second set of values for the implant position parameters, and wherein the second position is different to the first position; determining an indication of any differences between the planned position of the implant and the actual intra-operative position of the implant using at least one of the first set of distances and the second set of distances, and distances that have been intra-operatively measured from the implant to the anatomical features of the bone of the patient, and storing at least one of the first set of distances and the second set of distances in a computer readable medium.

2. The method of claim 1, wherein the number of anatomical features is at least the same as, or greater than, the number of implant position parameters.

3. The method of claim 1, wherein the implant position parameters include at least one distance and at least one angle.

4. The method of claim 1, further comprising the step of repeating the the first calculating step and the second calculating step for a range of values of each of the implant position parameters.

5. The method of claim 1, wherein determining an indication of any differences includes the step of identifying the calculated distances for an implant position that most closely match the measured distances for the implant position.

6. The method of claim 5, further comprising the step of determining the values of the implant position parameters corresponding to the most closely matching calculated distances.

7. The method of claim 6, further comprising the step of determining the differences between the values of the implant position parameters for the planned position of the implant and the values of the implant position parameters for the intra-operative position of the implant.

8. The method of claim 7, further comprising the step of outputting the differences between the values of the implant position parameters for the planned position of the implant and the values of the implant position parameters for the intra-operative position of the implant.

9. The method of claim 8, further comprising the step of automatically determining an adjustment to be made to the implant in order to bring the intra-operative position of the implant closer to the planned position of the implant using the outputted differences.

10. The method of claim 1, further comprising the step of outputting the values of the implant position parameters for each different position of the implant relative to the three dimensional bone model together with the corresponding distances from the implant to the plurality of anatomical features.

11. The method of claim 10, wherein the values of the implant position parameters and the corresponding distances are arranged in a look up table, in which the values of the implant position parameters are indexed by the distances.

12. The method of claim 1, wherein the bone of the patient is a femur and the implant is a stem implant component.

13. The method of claim 12, wherein the implant position parameters include depth, varus-valgus angle and retroversion-anteversion angle.

14. The method of claim 12, wherein the plurality of anatomical features include at least three anatomical features selected from: the anterior aspect of the greater trochanter; the posterior aspect of the greater trochanter; the superior aspect of the intertrochanteric line; the quadrate tubercle on the intertrochanteric crest; and the lesser trochanter.

15. A method for determining the intra-operative deviation from a planned implant position, comprising the steps of: generating a three dimensional model of at least a surface of a bone of a patient into which an implant is to be implanted, the three dimensional model including a plurality of anatomical features of the bone; creating a planned position of the implant in the patient's bone from the three dimensional model; calculating a first set of distances, the first set of distances being measured from a plurality of anatomical features present in a three dimensional model of at least the surface of the bone of the patient relative to a model of the implant at a first position in the three dimensional model of the bone, the first position corresponding to a first set of values for the implant position parameters; calculating a second set of distances, the second set of distances being measured from the plurality of anatomical features present in the three dimensional model to a model of the same implant at a second position in the three dimensional model of the bone, the second position corresponding to a second set of values for the implant position parameters, and wherein the second position is different to the first position; and using the determined distances and distances of the plurality of anatomical features relative to the implant that have been intra-operatively measured to determine an indication of any differences between the planned position of the implant and the actual intra-operative position of the implant in the bone using at least one of the first set of distances and the second set of distances, and distances that have been intra-operatively measured from the implant to the anatomical features of the bone of the patient; and storing at least the determined distances in a computer readable medium.

16. The method of claim 15, further comprising the step of tracking the position of a trackable instrument and determining the distances that have been intra-operatively measured from the tracked positions of the trackable instrument.

17. The method of claim 15, further comprising the step of using a caliper to measure the distance of each of the anatomical features relative to the implant.

18. The method of claim 15, further comprising the steps of:
   attaching a measurement instrument to the implant; and
   adjusting the measurement instrument to directly or indirectly measure the distance to each of the anatomical features relative to the implant.

19. The method of claim 18, further comprising the step of adjusting the angular position and/or the length of at least a part of the instrument.

20. The method of claim 15, further comprising the step of configuring an adjustable implant so as to compensate for or reduce a difference in the planned position of the implant and the intra-operative position of the implant in the bone.

* * * * *